United States Patent
Glas et al.

(10) Patent No.: US 10,021,848 B2
(45) Date of Patent: Jul. 17, 2018

(54) METHOD FOR PROVIDING CYTOPLASMIC MALE STERILE PETROSELINUM CRISPUM PLANTS, CYTOPLASMIC MALE STERILE PETROSELINUM CRISPUM PLANTS AND SEEDS AND PLANT PARTS THEREOF

(71) Applicant: Bejo Zaden B.V., Warmenhuizen (NL)

(72) Inventors: Cornelis Glas, Tuitjenhorn (NL); Nicolas Johannes Dol, Spanbroek (NL); Witte Van Cappellen, Broek op Langedijk (NL); Albertus Johannes Maria Schrijver, Warmenhuizen (NL)

(73) Assignee: BEJO ZADEN B.V, Warmenhuizen (NL)

( * ) Notice: Subject to any disclaimer, the term of this patent is extended or adjusted under 35 U.S.C. 154(b) by 76 days.

(21) Appl. No.: 14/646,521

(22) PCT Filed: Nov. 22, 2012

(86) PCT No.: PCT/EP2012/073328
§ 371 (c)(1),
(2) Date: May 21, 2015

(87) PCT Pub. No.: WO2014/079498
PCT Pub. Date: May 30, 2014

(65) Prior Publication Data
US 2015/0296734 A1 Oct. 22, 2015

(51) Int. Cl.
| | | |
|---|---|---|
| *A01H 5/12* | (2018.01) | |
| *A01H 1/02* | (2006.01) | |
| *C12N 5/14* | (2006.01) | |
| *C12N 15/02* | (2006.01) | |
| *A01H 1/06* | (2006.01) | |

(52) U.S. Cl.
CPC ............... *A01H 5/12* (2013.01); *A01H 1/02* (2013.01); *A01H 1/06* (2013.01); *C12N 5/14* (2013.01); *C12N 15/02* (2013.01)

(58) Field of Classification Search
None
See application file for complete search history.

(56) References Cited

PUBLICATIONS

Quagliotti et al. Eucarpia, Fifth Congress of the European Association for Research on Plant Breeding, pp. 359-363 (1969).*
Ramanujam et al. Indian Journal of Genetics and Plant Breeding 30(3): 732-737 (1970).*
Pank et al. Zeitschrift fur Arnzei und Gewurzpflanzen 12: 88-94 (2007).*
Miura et al. Plant Cell Reports 5: 310-313 (1986).*
Watin et al. Comptes Rendus de l'Academie des Sciences, Serie III: Sciences de la Vie; 309(16): 653-659 (1989) Abstract Only.*
Watin et al. Comptes Rendus de l'Academie des Sciences, Serie III: Sciences de la Vie; 309(16): 653-659 Document (1989) Full Document.*
Astley, D. "Report of a Workshop on Umbellifer Crops Genetic Resources"; IPGRI; Aug. 31, 1997; Krakow, Poland.
Liu, Jihong, et al. "Intergeneric Somatic Hybridization and its Application to Crop Genetic Improvement"; Plant Cell, Tissue and Organ Culture; vol. 82, pp. 19-44 (2005).
Melchers, Georg, et al. " One-Step Generation of Cytoplasmic Male Sterility by Fusion of Mitochondrial-Inactivated Tomato Protoplasts with Nuclear-Inactivated Solanum Protoplasts"; Plant Biology: vol. 89; Aug. 1992; pp. 6832-6836, (PNAS).
Dudits, Denes, et al. "Intergeneric Gene Transfer Mediated by Plant Protoplast Fusion"; Molec. Gen. Genet.; vol. 179, pp. 283-288, 1980
Saccardo, F., et al. "New Fennel Hybrids Production for Improving Bulb Yield and Quality"; Mar. 2000, Atti v Giornate Scientifiche, vol. 1, p. 159-160.
Fang, Tan, et al. "Preliminary Study of Asymmetric Protoplast Fusion Between Celery and CMS Carrot"; 2009, Acta Horticulture Sinica 36: 116-976.

* cited by examiner

*Primary Examiner* — David T Fox
(74) *Attorney, Agent, or Firm* — Nath, Goldberg & Meyer; Joshua B. Goldberg; Tanya E. Harkins (57) ABSTRACT

The present invention relates to methods for providing cytoplasmic male sterile *Petroselinum* plants, cytoplasmic male sterile *Petroselinum crispum* plants and to seeds, cells, tissues and plant parts thereof. Specifically the present invention relates to a method for providing a cytoplasmic male sterile *Petroselinum crispum* plant comprising: (a) providing first protoplasts obtained from a plant selected from the group consisting of *Daucus carota* L., *Foeniculum vulgare* Mill., *Apium graveolens* L., and *Pastinaca sativa* L., wherein the first protoplasts have a substantially inactivated nuclear genome and a substantially non-modified cytoplasm; (b) providing second protoplasts obtained from *Petroselinum crispum* wherein the second protoplasts have a substantially inactivated cytoplasm and a substantially non-modified nuclear genome; (c) fusing said first and second protoplasts; and (d) obtaining from the fusion product of said first and second protoplasts a cytoplasmic male sterile *Petroselinum crispum* plant.

6 Claims, 4 Drawing Sheets

Figure 4

SEQUENCE LISTING

```
<160> NUMBER OF SEQ ID NOS: 5

<210> SEQ ID NO 1
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="sequence P3558 primer"
      /organism="artificial sequences"

<400> SEQUENCE: 1
caaaagtatg aaaagctgga gg                                              22

<210> SEQ ID NO 2
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="sequence P7054 primer"
      /organism="artificial sequences"

<400> SEQUENCE: 2 cctttttga tcccgctgga gg                                               22

<210> SEQ ID NO 3
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="sequence P10987 primer"
      /organism="artificial sequences"

<400> SEQUENCE: 3
cccaatcttt aaggaagaga tcg                                             23

<210> SEQ ID NO 4
```

```
<211> LENGTH: 22
<212> TYPE: DNA
<213> ORGANISM: artificial sequences
<220> FEATURE:
<221> NAME/KEY: source
<222> LOCATION: 1..22
<223> OTHER INFORMATION: /mol_type="DNA"
      /note="sequence P10988 primer"
      /organism="artificial sequences"

<400> SEQUENCE: 4
atgtctccgt cgctgacgtt cg                                              22

<210> SEQ ID NO 5
<211> LENGTH: 23
<212> TYPE: DNA
<213> ORGANISM: artificial sequences
<220> FEATURE:
<221> NAME/KEY: source
<222> LOCATION: 1..23
<223> OTHER INFORMATION: /mol_type="DNA"
      /note="sequence P11087 primer"
      /organism="artificial sequences"

<400> SEQUENCE: 5
gtacgataga attcctcggt gcg                                             23
```

METHOD FOR PROVIDING CYTOPLASMIC MALE STERILE PETROSELINUM CRISPUM PLANTS, CYTOPLASMIC MALE STERILE PETROSELINUM CRISPUM PLANTS AND SEEDS AND PLANT PARTS THEREOF

CROSS-REFERENCE TO PRIOR APPLICATION

This is a National Phase Application filed under 35 U.S.C. 371 as a national stage of PCT/EP2012/073328, filed on Nov. 22, 2012, the entire content of which is hereby incorporated by reference in its entirety.

BACKGROUND

The present invention relates to methods for providing cytoplasmic male sterile *Petroselinum crispum* plants, cytoplasmic male sterile *Petroselinum crispum* plants and to seeds, cells, tissues and plant parts thereof.

The Sequence Listing submitted in text format (.txt) filed on May 21, 2015, named "2NJ60_5-20-2015.txt", (created on May 20, 2015, 2 KB), is incorporated herein by reference.

*Petroselinum crispum* or parsley belongs to the Umbelliferae or Apiaceae family. Members of this family are flat leaf parsley (*P. crispum* var. *neapolitanum*), curly leaf parsley (*P. crispum* var. *crispum*) and Hamburg parsley or rooted parsley (*P. crispum* var. *tuberosum*).

Leaf type parsley is often used as a garnish and has a typical flavour caused by volatile oils like myristicin and flavonoids as apiin.

Rooted parsley has a long, fleshy, white taproot generally served as a vegetable or used in soups or stews. The root is rich in carotene, vitamins B2 and C. The leaves of the plant are prepared in a similar way as of leaf type parsley. Rooted parsley is especially popular in Germany, Austria, Hungary and Russia. In Western Europe the crop is rediscovered, particularly in organic horticulture.

Other members of the Umbelliferae family are, for example, parsnip (*Pastinaca sativa*), carrot (*Daucus carota* L.), celery (*Apium graveolens* L.), fennel (*Foeniculum vulgare* Mill.), caraway (*Carum carvi*), anise (*Pimpinella anisum*), dill (*Anethum graveolens*) and coriander (*Coriandrum sativum*).

For cultivation of parsley, presently, only open pollinated crossbred races are available. As a result of the absence of male sterility or, for example, self-incompatibility of the crop, it is impossible to develop F1 hybrids.

F1 hybrids in general have advantages over open pollinated crops. According to the handbook "Principles of Plant Genetics and Breeding" by G. Acquaah (Blackwell Publishing, ISBN-13: 978-1-4051-3646-4; 2007; chapter 18) a hybrid cultivar is the F1 offspring of a planned cross between inbred lines. A critical requirement of hybrids production is that the parents are unidentical. This divergence gives hybrids their superior performance, due to the exploitation of heterosis or hybrid vigor. Hybrid vigor may be defined as the increase in size, vigor, fertility and overall performance of a hybrid plant over the average performance of the two parents (Ibid. pages 334-335).

The availability of F1 hybrids in parsley is considered advantageous over the present open pollinated crossbred races in a number of ways. F1 hybrids, as compared to the available open pollinated races, generally have an improved emergence, higher yields, more vigour and/or a high uniformity.

In general, F1 hybrids of a crop can be produced by the use of male sterile parent lines which are, inherently, unable to self-pollinate and are used as mother lines. An alternative, known for example from *Brassica* crops, is the use of self-incompatible plants which cannot self-pollinate and therefore make the production of F1 hybrids possible.

Male sterile parent lines provide control over the genetic composition of the progeny since the inheritance of traits is, in principle, fixed. Half of a progeny's nuclear genetic material, i.e. nuclear genome, originates from the male parent line (male fertile), while the other half of a progeny's nuclear genetic material, i.e. nuclear genome, originates from the female (male sterile) parent line from which the F1 seed is harvested.

Parsley plants, however, generally are both male and female (i.e. monoecious) and the absence of male sterile parent plants, such as in open pollinated crossbred races, makes a 100% reliable prediction of the genetic makeup, or (nuclear) genotype of the progeny impossible. At least some progeny, in the absence of male sterile plants, as a result of self-pollination, comprise the genetic material, or nuclear genome, originating from only one parent line.

The term hybrid, F1 hybrid or cybrid is often used in the art to denote that the plants concerned are heterozygous for at least some (commercially interesting) genotypic traits. Generally, a hybrid, F1 hybrid or cybrid is denoted in the art as comprising a heterozygous nuclear genome.

Male sterility in plants generally relates to cytoplasmic male sterility, wherein the determining genetic factor is located in the cytoplasm. For many plants it is demonstrated that this determining genetic factor is comprised in the mitochondria and generally encompasses a mutation in mitochondrial DNA.

Mitochondria are only inherited by the progeny through the egg cell or, in other words, by female inheritance, and not by the pollen, or, in other words, by male inheritance. Cytoplasmic male sterility is also designated in the art with the abbreviation CMS.

In some plants, besides cytoplasmic male sterility, also nuclear (male) sterility is observed. For nuclear (male) sterility, in contrast to cytoplasmic encoded sterility, a genetic factor in the nuclear genome, or the DNA of the nucleus, is responsible for the observed sterility. This nuclear sterility may relate to male, female or general sterility.

Both types of sterility, i.e. cytoplasmic male sterility and nuclear (male) sterility can easily be distinguished. Cytoplasmic male sterility is only inherited through the female parent line. In contrast, as an inherent result of its presence in the nucleus, nuclear sterility generally shows a Mendelian inheritance.

Through the use of CMS, cross pollination will result in 100% "pure" or "true" F1 hybrids. In contrast, using normal monoecious parsley plants, a certain percentage of self-pollination will occur in the next generation.

Fennel is a species within the Apiaceae family where CMS is a common trait, the use of F1 hybrids in fennel is generally known. In fennel, no genes are known which restore fertility; therefore it is an ideal source of CMS.

It was demonstrated that it was possible to obtain a cross between parsley and fennel. In other words, a cross wherein one parent line, the pollinator, is parsley and the other parent line is CMS fennel. However, this cross appeared to be very inefficient; instead of the expected amount of at least 2500 seeds only a very limited amount of seeds could be obtained by flowering these plants in the presence of blowflies. Most of these seeds were non-viable as well. After germination of the seed the desired progeny was indeed obtained.

Although, eventually aided by embryo rescue, this progeny obtained can be crossed further with parsley, thereby diluting the amount of fennel nuclear genome, after several generations of backcrossing an inbred generation, made by self-pollination, is required.

Using an inbred generation, it is in principle possible to select progeny having the desired phenotype (a parsley genome without fennel characteristics). Despite this, a large number of generations will still comprise small amounts of fennel DNA, causing undesired characteristic or traits in the hybrid obtained. It cannot be predicted at which point in time this remaining fennel DNA will be eliminated from the nuclear genome.

However, with the present case of cytoplasmic male sterile (CMS) fennel, the required inbred generation of a fennel-parsley hybrid is not possible because the plants needed for this surely are male sterile, therefore making an inbred generation technically impossible.

Considering, amongst others, the above advantages of F1 hybrids, such as an improved emergence, higher yields, more vigour and/or a high uniformity, there is a need in the art to provide cytoplasmic male sterile (CMS) *Petroselinum crispum* plants. Accordingly, it is an object, amongst other objects, of the present invention to fulfil this need.

BRIEF DESCRIPTION

The above need, amongst other needs, is fulfilled according to a first aspect of the present invention, by providing a method for providing a cytoplasmic male sterile *Petroselinum crispum* plant comprising:
  a) providing first protoplasts obtained from a plant selected from the group consisting of *Daucus carota* L., *Foeniculum vulgare* Mill., *Apium graveolens* L., and *Pastinaca sativa* L., wherein the first species of protoplasts have a substantially inactivated nuclear genome and a substantially non-modified cytoplasm as compared to the plant cells from which they are derived; these first protoplasts may also be designated as donor protoplasts;
  b) providing second protoplasts obtained from a *Petroselinum crispum* plant wherein the second protoplasts have a substantially inactivated cytoplasm and a substantially non-modified nuclear genome as compared to the plant cells from which they are derived; these second protoplasts may also be designated as acceptor protoplasts;
  c) fusing said first and second protoplasts to provide a fusion product between the acceptor protoplast and the donor protoplast;
  d) obtaining a cytoplasmic male sterile *Petroselinum crispum* plant from the fusion product of said first and second species of protoplasts, and, optionally,
  e) obtaining a F1 hybrid by crossing the obtained cytoplasmic male sterile *Petroselinum crispum* plant of step (d) with a monoecious *P. crispum* plant.

DETAILED DESCRIPTION

Within the context of the present invention, hybrid, hybrid F1 or cybrid plants are plants which at least comprise heterologous or foreign organelles such as mitochondria or chloroplasts. In other words, these hybrid, hybrid F1 or cybrid plants comprise organelles originating from another plant variety and these organelles are not found in these plants naturally. Hybrid, hybrid F1 or cybrid plants may also be designated as plants which comprise at least partially a cytoplasm which originates, or is obtained, from another variety or species.

The genotype of the nucleus of the plants according to the present invention is substantially identical to one of the parent plants, namely the acceptorplant. However, the DNA of the cytoplasm of the plants according to the present invention deviates from this parent plant. This cytoplasm is at least partially obtained from another parent plant, the donorplant. This other parent plant is a plant of another variety or species than the first parent plant.

Techniques and methods for providing protoplasts, i.e. plant cells with an at least partially removed cell wall, are known in the art. In general, protoplasts are obtained by digestion of isolated plant cells, or tissues, with a mixture of suitable polysaccharide degrading enzymes, such as cellulases, pectinases and/or xylanases.

Techniques and methods for fusing, or combining, of the present protoplasts are known in the art. Protoplast fusion can, for example, be provided by combining the present protoplasts in a mixture and subsequently exposing this mixture to an electroshock or exposing of this mixture to a composition comprising a polymer, such as polyethylene glycol, and a cation, such as $Ca^{2+}$, with an alkaline pH.

Techniques and methods for providing plants from the present fusion product are known in the art. The present fusion product may, for example, be stimulated by use of hormones to generate cell walls, subsequently to form callus and regenerate into complete plants. The provision may, optionally, as is for example the case for providing a F1 hybrid, comprise one or more conventional crossing steps, preferably with parsley varieties of commercial interest.

The term "inactivated nuclear genome", within the context of the present invention, denotes a nuclear genome which is no longer capable of mitosis and/or meiosis. In other words, a protoplast, or a plant cell derived thereof, with an "inactivated nuclear genome" is no longer capable of cell division. The present inactivation of the nuclear genome may, for example, be provided by the use of a radiation treatment of the present protoplasts with Röntgen (X) or gamma (γ) radiation. Alternatively, the nucleus of the cell can be removed by ultracentrifugation in a density gradient.

The term "inactivated cytoplasm", within the context of the present invention, denotes that the organelles in the cytoplasm are no longer capable of participating in cell division. In other words, a protoplast, or a plant cell derived thereof, with an "inactivated cytoplasm" is no longer capable of cell division. The present inactivation of the cytoplasm may, for example, be provided by subjecting the present protoplasts to reagents such as iodoacetamide or iodoacetate.

The term "non-modified cytoplasm", within the context of the present invention, denotes that the cytoplasm is substantially similar to the cytoplasm of the starting cell. In other words, protoplasts with a "non-modified cytoplasm" are regarded as the original cytoplasm, indistinguishable from the cell from which the protoplast is derived.

The term "non-modified nuclear genome", within the context of the present invention, denotes that the nuclear genome is substantially similar to the nuclear genome of the starting cell. In other words, protoplasts with a "non modified nuclear genome" are regarded as to possess the original nuclear genome, indistinguishable from the nuclear genome of the cell from which the protoplast is derived.

Through the use of the present method, the nuclear encoded genetic composition, or nuclear genome, of the second protoplasts does not change substantially. As a result, a cytoplasmic male sterile *Petroselinum crispum* plant is provided directly, without the necessity of further (back) crossing steps.

However, additional crossing steps may be used to add further (commercial interesting) traits to the present cytoplasmic male sterile *Petroselinum crispum* plant. These crossings are also encompassed by the present invention, provided that the progeny remains cytoplasmic male sterile.

According to a preferred embodiment of the present invention, the donor plant, selected from the group consisting of *Daucus carota* L., *Foeniculum vulgare* Mill., *Apium graveolens* L., and *Pastinaca sativa* L., has a cytoplasmic male sterile phenotype.

According to a further preferred embodiment of the present method, the method further comprises, after step (c) or (d), selecting diploid fusion products and/or diploid plants.

In a number of cases, some fusion products and/or plants obtained after protoplast fusion have a deviant ploidy level, such as a tetraploid, octaploid and sometimes aneuploid level. These deviations often result in undesired plants, such as female sterile plants. Therefore, it is advantageous to select only those fusion product and/or plants, for example by flowcytometry, which are, with respect to their nuclear DNA content, similar to the diploid acceptor plant.

Further, flowcytometry provides the possibility to detect and subsequently eliminate occurring genetic deviations, such as unexpected and undesired nuclear genomic material from the first protoplasts appearing in the fusion product.

According to yet another preferred embodiment of the present method, the above described first protoplasts are obtained from *Foeniculum vulgare* Mill., preferably from a cytoplasmic male sterile *Foeniculum vulgare* Mill. plant.

According to another preferred embodiment of the present method, the above described first protoplasts having a substantially inactivated nuclear genome and a substantially non-modified cytoplasm are obtained by an exposure to ionising radiation, preferably a gamma-radiation dosage, of at least 200 Gray (Gy), preferably at least 300 Gray, and more preferably at least 400 Gy.

According to yet another preferred embodiment of the present method, the above described second protoplasts have a substantially inactivated cytoplasm and a substantially non-inactivated nuclear genome through an exposure to iodoacetamide, preferably in a concentration of at least 5 mM, more preferably at least 10 mM, most preferably at least 15 mM.

According to a preferred embodiment of the present method step (c) comprises polyethylene glycol mediated protoplast fusion.

The present method advantageously provides cytoplasmic male sterile *Petroselinum crispum* plants. Consequently, according to a further aspect, the present invention relates to cytoplasmic male sterile *Petroselinum crispum* plants obtainable by the present method, comprising mitochondria and/or chloroplasts obtained from a plant, preferably a cytoplasmic male sterile plant, selected from the group consisting of *Daucus carota* L., *Foeniculum vulgare* Mill., *Apium graveolens* L., and *Pastinaca sativa* L, preferably comprising mitochondria and/or chloroplasts obtained from *Foeniculum vulgare* Mill.

According to a preferred embodiment of this aspect, the first protoplast is obtained from a *Foeniculum vulgare* Mill. plant with the deposit number NCIMB 42055 (deposited on Sep. 26, 2012 at NCIMB Ltd, Ferguson Building, Craibstone Estate, Bucksburn, Aberdeen) and/or the second protoplast is obtained from a *Petroselinum crispum* var. *tuberosum* plant with the deposit number NCIMB 42056 (deposited on Sep. 26, 2012 at NCIMB Ltd).

According to yet another aspect, the present invention relates to the use of a cytoplasmic male sterile *Petroselinum crispum* plant according to the present invention for providing *Petroselinum crispum* F1 hybrids.

According to still another aspect, the present invention relates to seeds, plant parts, tissue or cells obtained from, or originating from, the present CMS parsley plant as described above.

According to yet another further aspect, the present invention relates to the use of the cytoplasm obtained from a plant, preferably cytoplasmic male sterile, selected from the group consisting of *Daucus carota* L., *Foeniculum vulgare* Mill., *Apium graveolens* L., and *Pastinaca sativa* L., preferably *Foeniculum vulgare* Mill., for providing a cytoplasmic male sterile *Petroselinum crispum* plant.

The present invention is further detailed in the following examples of preferred embodiments.

EXAMPLES

Example 1: General Protocol

Seeds from *P. crispum* var. *tuberosum* (acceptor) as well as seeds from a donor plant were sterilized by a subsequent treatment with hot water, washing with 70% ethanol and a treatment with diluted domestic bleach. After rinsing the seeds with sterile water, the seeds were germinated on a MS30 or similar medium.

Only the petioles from the seedlings were used. Protoplasts were isolated by treating the material after pre-plasmolysis with cell wall degrading enzymes such as pectinase and cellulase, in a plasmolysing solution. After filtration and centrifugation, the protoplasts of the donor were treated with gamma radiation. The protoplasts of the acceptor were treated with iodoacetamide (IOA). Both species of protoplasts were combined and subsequently fused. During polyethylene glycol (PEG) mediated fusion the protoplasts were not agitated, in order to avoid disruption of the fusion process.

After fusion, PEG was gradually washed out and the protoplasts were embedded in alginate. Slices of alginate solidified medium, which include the fused protoplasts, were transferred into a liquid medium stimulating cell division. In this medium sugar as glucose and hormones as 2.4D, zeatine and the like were present.

After the emergence of callus, micro-calli were removed from the alginate solidified medium and transferred to a solid callus growth medium. After reaching a diameter of 8 mm and a certain degree of greening, the calli were transferred to a regeneration medium. Regenerating calli were transferred onto fresh regeneration medium every 3 weeks. On this medium stem cuttings and sometimes somatic embryos developed. The developed stem cuttings were placed on a rooting medium BBW. Somatic embryos were placed on an embryo growth medium and afterwards placed on a MS30 or similar medium.

During the transition from the cell division medium (CPP) via the growth out medium (CPPD) onto the regeneration medium (M2+) and finally MS30 medium the osmotic value of the medium was gradually decreased.

The ploidy level of the plants obtained was examined by determining the relative DNA content by flowcytometry of a leaf sample. Plants with a relative DNA content which corresponds to the DNA content of the original parsley plants were retained; all other plants were destroyed.

The retained plants were further analysed by use of molecular biological techniques. Using DNA isolated from a leaf, the presence of the desired mitochondria (i.e. from the donor) was checked by PCR primers being specific for fennel mitochondrial DNA. Plants with the cytoplasm of the acceptor (which can be regarded as escapees) were discarded.

The remaining plants were maintained by crossings and, under greenhouse and field conditions, examined for their practicability. Characteristics of interest were male sterility, seed formation and quality of the plant.

Example 2: Surface Sterilization of Seed

Seeds from rooted parsley (*Petroselinum crispum* var. *tuberosum*) as acceptor and from fennel (*Foeniculum vulgare* Mill.) as donor were each put into separate tea sieves. The sieves were placed in a water bath of 50° C. for 10 min. Subsequently, the tea sieves were dipped in a mixture consisting of 70% ethanol and 30% water for 10 seconds. This was followed by a 20 min. treatment with 0.3% (w/v) NaOCl+0.01% Tween80. This and all following treatments were performed in a laminar flowcabinet.

Subsequently, the tea sieves with seeds where washed 3 times with sterile water, during 1, 3 and 5 minutes respectively.

Example 3: Sowing of the Starting Material for Protoplast Isolation

Seeds of the acceptor and donor were taken from the tea sieves of example Example 2 under sterile conditions and placed onto MS30 medium in glass containers. The containers, with 8 seeds each, were placed in a climate room at 25° C. (16 hours light, 4000 lux). After 3 to 5 weeks, the germinated plants were suitable for protoplast isolation.

Example 4: Protoplast Isolation

The petioles of the germinated acceptor plants were collected in a 9 cm 0 Petri dish with 15 ml MLP. When all petioles were collected, these petioles were cut into pieces with an average length of 1.5 mm.

Petioles of the germinated donor plants were also collected and cut in MLP. However, when the amount of available material was insufficient (for instance as a result of a poor emergence of the seed), the leaves themselves were added.

The MLP solution was removed by aspiration and replaced by 20 ml fresh enzyme solution per Petri dish. This enzyme solution has a high specific gravity in relation to the protoplasts. The Petri dishes were incubated at 25° C. overnight in the dark; they were placed on an orbital shaker with an amplitude of 15 mm and a speed of 30 rpm. After this incubation, the suspensions were filtered through nylon filters with a pore size of 110 μm en 53 μm respectively. The filtrate was transferred into 12 ml centrifugation tubes, wherein 8 ml filtrate was transferred per tube.

Onto this layer of enzyme-protoplasts suspension 3 ml wash solution W5 (with a lower specific gravity) was carefully pipetted, followed by a centrifugation of 7 min. at 100×g. After centrifugation, bands of pure protoplasts were visible in the tubes (at the interface of enzyme and wash solution). Damaged protoplasts, cell walls and the like were collected at the bottom of the tube.

The band containing protoplasts was collected using a pipette and a maximum of 4 ml suspension was collected in new tubes. To these tubes additional wash solution W5 was added to a final volume of 12 ml. The tubes were centrifuged again during 7 min. at 100×g and, afterwards, the washed protoplasts became visible as a pellet at the bottom of the tube. The supernatant liquid was poured off and the protoplasts were carefully re-suspended in 11 ml end volume wash solution W5.

From each suspension (donor and acceptor) 1 ml was taken apart as control; a sample from this control was counted using a haemocytometer for determining the total number of protoplasts isolated.

The tube with protoplasts of the donor was wrapped in aluminium foil and placed on ice. Gamma radiation was performed using a radiation dosage of 400 Gy. After the radiation, a sample was cultured separately as control.

The protoplasts of the acceptor were treated as follows: from an appropriate stock solution in W5 IOA was added to a final concentration of 15 mM. The incubation was performed at room temperature; the incubation was terminated by centrifugation of the protoplasts, pouring off of the supernatant and re-suspending of the protoplasts in wash solution W5. The total amount of time of incubation was 15 min. including the time of centrifugation.

Subsequently, the acceptor protoplasts were washed once with wash solution W5 by centrifugation. After this IOA treatment a control sample of the treated cells is taken and cultured separately.

Example 5: Protoplast Fusion

From both protoplast suspensions, protoplasts were mixed in a 1 acceptor: 2 donor protoplast ratio. This suspension was divided over sufficient 10 ml test tubes, in such a way that each test tube contained 1 million protoplasts.

After centrifugation (7 min. at 100×g) the volume was adjusted to 0.3 ml. To this protoplast suspension, 400 μl PEG solution was added. The tubes with protoplasts were allowed to stand for 30 min. without disturbance. Subsequently, 800 μl of PEG dilution solution was added, followed by a waiting step of 15 min.

Next, 5 ml of CPW/$Ca^{++}$-solution was added to each tube followed by centrifugation (7 min. at 100×g; without braking afterwards). The supernatant was carefully poured off and the pellet was re-suspended in 5 ml fresh CPW/$Ca^{++}$-solution and centrifuged again under the same conditions.

After removal of the supernatant, the pellet was re-suspended in 10 ml solution adjusted solution A per tube. The cells were washed by centrifugation, re-suspended in adjusted solution A en centrifuged again as described above. Finally, the cells were combined in 1 or, when necessary, more test tubes of 50 ml en re-suspended in adjusted solution A until a density of 400.000 cells per ml was reached.

To this suspension, an equal volume of alginate solution was added and, subsequently, the suspension was plated out in 800 µl portions on small Petri dishes (Ø6 cm) with solution B. After 1 hour the droplets were solidified by polymerization of alginate.

Example 6: Regeneration

The alginate slices with fused protoplasts were washed in the CPP medium and transferred to Petri dishes with fresh CPP medium; per slice of 800 µl 5 ml CPP medium was used. Weekly, the complete medium was refreshed by removing the old medium by aspiration and adding fresh medium to the Petri dishes. After approximately 3 weeks, calli were generated. The moment these calli reached a diameter of approximately 3 mm, they were removed from the alginate. To this end, the slices were cut in 8 parts and the medium was replaced by 15 ml 50 mM Na-citrate solution. The Petri dishes were placed on an orbital shaker with an amplitude of 15 mm and a speed of 30 rpm.

After 1 hour, the alginate matrix was disrupted and the calli were released and collected by centrifugation (7 min. at 100×g) and placed on a solid CPPD medium. After 1 week of habituation the Petri dishes were placed in light. Each 3 weeks, the growing calli were transferred to fresh medium. The moment the calli greened and reached a diameter of approximately 8 mm, they were placed on regeneration medium M2+. Again, each 3 weeks the medium was refreshed by transferring the calli to new Petri dishes with the same medium.

Stem cuttings which generated on the medium were rooted on BBW medium. The somatic embryos which emerged were placed on MS20-GA3 medium. Mature plants grown on this medium were transferred to MS20 medium. When the rooted plants reached the 3-leaf stage, they were transferred to soil for further development in a greenhouse.

Example 7: Flowcytometry

The ploidy level from regenerated plants was determined by flowcytometry. To this end, a sample of a known diploid plant was measured as a standard, and the samples of the regenerated plants were compared therewith. For each plant, a part of 1 cm$^2$ of the leaf was taken and cut in DAPI buffer (Partec, Munster, Germany) using a razor blade.

The sample was filtrated using a 30 µm CellTrics® filter (Partec) and measured with a Partec PA (Partec, Munster, Germany). The results provided a relative ploidy value in relation to the control. Only plants with a diploid rooted parsley pattern were used for further experimental work.

Example 8: Molecular Determinations

For plants with proven diploid character, the presence of the DNA fragment of interest (from fennel cytoplasm and therefore related to the desired CMS trait) was determined.

A sample of leaf, or callus, with a weight of 100 to 200 mg was frozen in an eppendorf tube at −20° C. After defrosting, the sample was crushed in 350 µl DNA extraction buffer. Subsequently, an additional amount of 350 µl DNA extraction buffer was added. After centrifugation (10 min. at 10.000×g) the supernatant was decanted and the pellet was transferred into 125 µl DNA extraction buffer; after thorough mixing 175 µl nuclei-lysis-buffer and 60 µl 10% N-lauryl sarcosine were added.

This mixture was incubated at 65° C. for 20 min., followed by extraction with 50-100 µl chloroform:isoamyl alcohol. The extract was centrifuged at 10.000×g for 10 min. and the supernatant was transferred into a new eppendorf tube. 500 µl isopropanol of −20° C. was added to this test-tube, and the tube was centrifuged at 10.000×g for 2 min.

After decanting the supernatant, the pellet was washed with 100 µl 70% ethanol (4° C.) and, after drying, the pellet was dissolved in 125 µl TE buffer. Finally, this DNA solution was diluted (10×) with sterile water.

The cytoplasmic DNA isolated was analysed by PCR techniques for the presence of the characterizing fragment. For each donor—acceptor combination, a protocol was developed providing a clear discrimination between both possible fusion partners.

TABLE 1

Primer combination yielding a polymorphism for parsley (acceptor) compared with several cytoplasm donors

| Donor: | Fennel<br>F. vulgare | Carrot<br>D. carota | Celery<br>A. graveolens | Parsnip<br>P. sativa |
|---|---|---|---|---|
| DNA | 2 µl | 2 µl | 2 µl | 2 µl |
| Invitrogen 10x PCR buffer | 2.5 µl | 2.5 µl | 2.5 µl | 2.5 µl |
| 50 mM MgCl$_2$ | 2.4 µl | 2.4 µl | 1.2 µl | 1.2 µl |
| NTP's | 0.3 µl | 0.3 µl | 0.6 µl | 0.3 µl |
| Primer (1 µl, 5 pM) | P3558 | P3558 | P10987 | P11087 |
| Primer (1 µl, 5 pM) | P7054 | P7054 | P10988 | P10988 |
| H$_2$O | 15.7 µl | 15.7 µl | 16.6 µl | 16.9 µl |
| Platinum Taq | 0.1 µl | 0.1 µl | 0.1 µl | 0.1 µl |
| Program | WP1 | WP1 | WP2 | WP2 |
| Digestion | MnlI | HinFI | Taq1 | AluI |

| program WP1 | | |
|---|---|---|
| 1 | 93° C. | 2 min |
| 2 | 62° C. | 1 min |
| 3 | 72° C. | 1.75 min |
| 4 | 93° C. | 30 seconds |
| 5 | 62° C. | 1 min |
| 6 | 72° C. | 1.75 min |
| 7 | repeat steps 4-6 39 times | |
| 8 | 72° C. | 5 min |
| 9 | 20° C. | 20 min |

| program WP2 | | |
|---|---|---|
| 1 | 94° C. | 5 min |
| 2 | 50° C. | 1 min |
| 3 | 72° C. | 1 min |
| 4 | 94° C. | 30 seconds |
| 5 | 50° C. | 1 min |
| 6 | 72° C. | 2 min |
| 7 | repeat steps 4-6 29 times | |
| 8 | 72° C. | 5 min |
| 9 | 20° C. | 20 min |

TABLE 2

Digestion of amplification products.

| | MnlI | HinFI | TaqI | AluI |
|---|---|---|---|---|
| DNA | 5 µl | 5 µl | 5 µl | 5 µl |
| NEB buffer 2 (10x) | 1.2 µl | 1.2 µl | — | 1.2 µl |
| NEB buffer 3 (10x) | — | — | 1.2 µl | — |
| BSA solution (100x) | 0.12 µl | — | 0.12 µl | — |

TABLE 2-continued

Digestion of amplification products.

|  | MnlI | HinFI | TaqI | AluI |
|---|---|---|---|---|
| enzyme | 2 units | 2 units | 2 units | 2 units |
| H$_2$O | 5.48 μl | 5.60 μl | 5.58 μl | 5.60 μl |
| Digestion-temperature | 37° C. | 37° C. | 65° C. | 37° C. |

Digestion took place during 8 hours at 37° C.

TABLE 3

| Sequence of the primers used | |
|---|---|
| P3558 | 5'-CAAAAGTATGAAAAGCTGGAGG-3' |
| P7054 | 5'-CCTTTTTTGATCCCGCTGGAGG-3' |
| P10987 | 5'-CCCAATCTTTAAGGAAGAGATCG-3' |
| P10988 | 5'-ATGTCTCCGTCGCTGACGTTCG-3' |
| P11087 | 5'-GTACGATAGAATTCCTCGGTGCG-3' |

Example 9: Gel Electrophoresis

Figure 1:
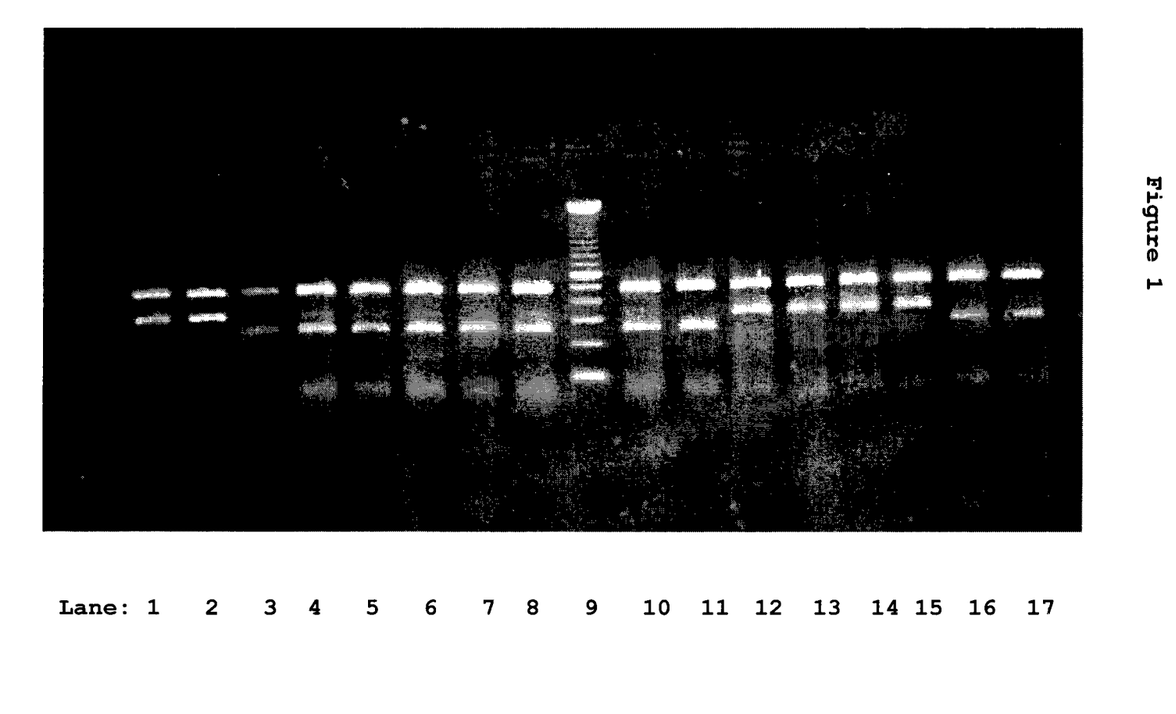
FIG. 1: shows an image of a gel electrophoresis of amplification products. Lanes 1 and 2 show "escapees", i.e. plants from a cell fusion showing a parsley cytoplasm pattern; the lanes 3-8, 10 and 11 show fusion plants according to the present invention, thus, parsley with a fennel cytoplasm; Lane 9 shows a DNA 100 bp ladder; lanes 12-15 show the original parsley acceptor material and the lanes 16 and 17 show the fennel donor material.

In case the difference in size between the fragments of a marker is sufficiently large, differences in band patterns of the individual plants can visualized by, for example, gel electrophoresis. The agarose gels used were composed of 1.5% agarose in TAE buffer and provided with ethidium bromide for visualization of the DNA bands using UV light. Representative results of such a gel electrophoresis of the amplification products obtained are shown in FIG. 1. FIG. 1 shows that plants according to the present invention (lanes 3-8, 10 and 11) provided a cytoplasmic amplification product with an identical size of the amplification product of the fennel donor plant, while the amplification product of the rooted parsley acceptor plant is absent. Accordingly, this demonstrates that the phenotypic rooted parsley plants according to the present invention have cytoplasm obtained from fennel.

Example 10: Hybrids

Ten selected rooted parsley plants J10666 and ten male sterile fennel plants J531 were vernalized in an enclosure free of frost during the winter. In the spring, these plants were transferred together into a greenhouse. After visual inspection of the first fennel inflorescences for male sterility, the plants were isolated in an insect tight enclosure. In these enclosures fly pupae were placed providing flies for pollination. When necessary, new fly pupae were introduced till the plants finished flowering.

Figure 2:
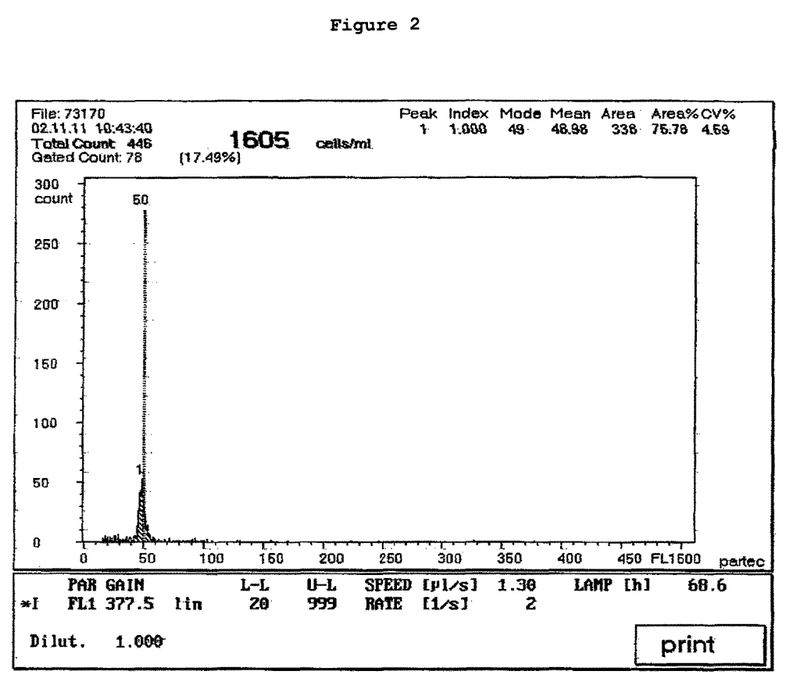
FIG. 2: shows a representative flowcytogram of fennel.
Figure 3:
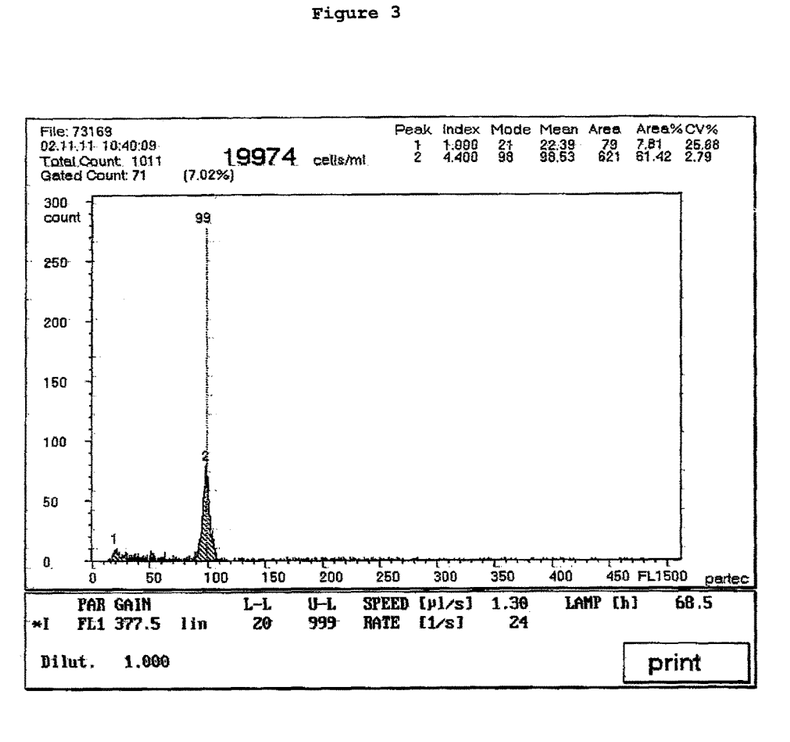
FIG. 3: shows a representative flowcytogram of parsley.
Figure 4:
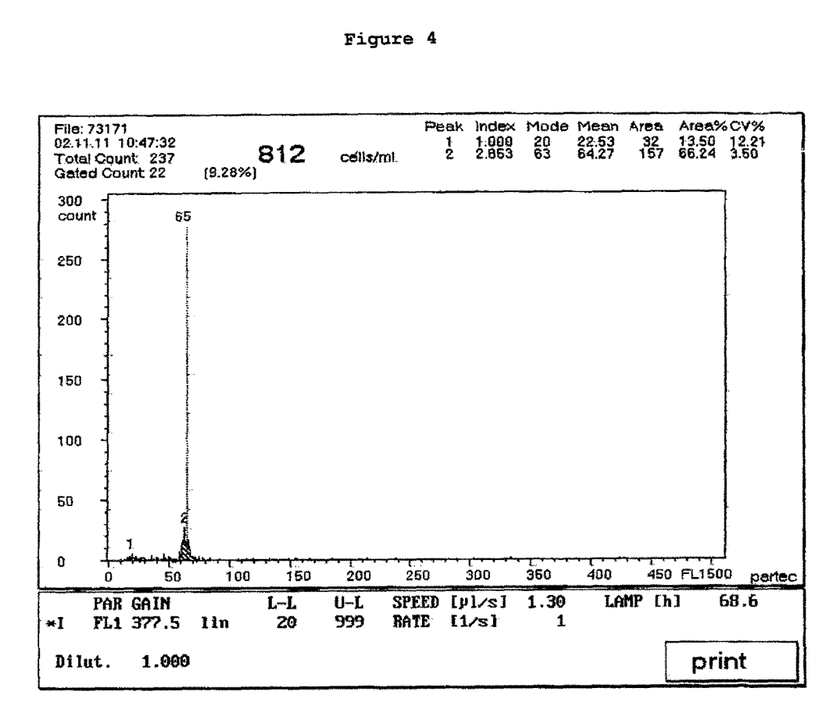
FIG. 4: shows a representative flowcytogram of a hybrid from fennel and parsley according to the present invention.

Seeds were harvested after maturation of male sterile fennel plants. The non-pollinated inflorescence of fennel control plants provided no seed. This demonstrated that these plants were indeed male sterile. Of all 39 seeds harvested only 1 seed germinated. Flowcytometric and molecular analysis showed that this plant indeed was an intermediate between fennel and rooted parsley. The results of flowcytometric analysis are shown in FIGS. 2 to 4, wherein the third image demonstrates the hybrid character of the plant identified.

Composition of the Media

Unless otherwise indicated, the media and solutions for tissue culture listed below were autoclaved (at 120° C. for 20 min.).

| MS20, MS30 medium | per liter |
|---|---|
| MS salts including vitamins (Duchefa, Haarlem, NL, art M0221) | 4.40 grams |
| Sucrose | 20 resp. 30 grams |
| Daichin agar | 8 grams | pH 5.8.

| Enzyme solution EKW solution comprising: | |
|---|---|
| Cellulase R10 | 1.5% |
| Macerozyme | 0.1% | pH 5.6; filter sterile

W5
L. Menczel, F, Nagy, Z. Kiss and P. Maliga. Theor. Appl. Genet 70: 590-594 (1981).

| PEG solution | |
|---|---|
| PEG6000 | 50 ml |
| | 15 grams |
| Sucrose | 2 grams |
| CaCl$_2$•2H$_2$O | 0.075 gram | pH 5.7; filter sterile

| PEG dilution solution | |
|---|---|
| Glycine | 50 ml |
| Glucose (Sigma) | 0.188 gram |
| CaCl$_2$•2H$_2$O | 2.7 grams |
| | 0.368 grams | pH 10.5 (adjusted with 10N KOH); 520 mOsm/kg; filter sterile

| CPW/Ca$^{++}$ | 200 ml |
|---|---|
| CPW 10 × stock | 20 ml |
| Mannitol | 13.3 grams |
| CaCl$_2$•2H$_2$O | 1.47 grams | pH 5.7; 530 mOsm/kg; filter sterile

CPW 10× stock solution
Frearson, E. M., Power, J. B., Cocking E. C. Developmental Biology, 33, 130-137 (1973)

| Adjusted solution A | 250 ml |
|---|---|
| CaCl$_2$•2H$_2$O | 36.8 mg |
| Mannitol | 19.7 grams | pH 5.8, autoclaved

Alginate solution; solution B
B. Damm, R. Schmidt and L. Willmitzer. Mol. Gen. Genet. 217: 6-12 (1989)
50 mM Na-citrate solution, MLP, EKW, CPP and CPPD
R. Dirks, V. Sidorov and C. Tulmans: Theor. Appl. Genet. 93: 809-815 (1996).
CPP medium is completed with 0.2 mg/l 2.4D and 0.1 mg/l zeatine.
CPPD medium is completed with 0.1 mg/l NAA and 0.2 mg/l zeatine.
M2+ medium per liter:
J. L. Vandemoortele, J. P. Billard, J. Boucaud and T. Gaspar (1994). Med. Fac. Landbouww. Univ. Gent 59: 1455-1459 (1994).
The M2 medium described is completed with 20 mg/l adenine sulphate and is denoted as M2+.

| BBW medium | per liter |
|---|---|
| MS salts (Duchefa art M0221) | 4.40 grams |
| Sucrose | 20 grams |
| IAA | 2 mgrams |
| Daichin agar | 8 grams | pH 6.0

| MS20-GA3 | per liter |
|---|---|
| MS salts (Duchefa art M0221) | 4.40 grams |
| Sucrose | 20 grams |
| GA$_3$ | 1 mgram |
| Daichin agar | 8 grams | pH 5.8 pH 5.8
DNA extraction buffer
0.35 M sorbitol
0.1 M Tris-base (pH 7.5)
0.005 M Na$_2$-EDTA
0.02 M NaHSO$_3$ (fresh added)
Nuclei-lysis Buffer
0.2 M Tris-base (pH 7.5)
0.05 M Na$_2$-EDTA
2 M NaCl
2% CTAB (cetyltrimethyl ammonium bromide)
Chloroform:isoamylalcohol
24 volumes chloroform+1 volume isoamylalcohol
TE buffer
10 mM Tris-NaOH (pH 8.0)
1 mM Na$_2$-EDTA
NEB buffer 2, NEB buffer 3 and BSA solution
Obtained from New England Biolabs, Ipswich, Mass.01938, USA
TAE buffer (final concentrations)
40 mM Tris-acetic acid, pH 8.5
2 mM Na$_2$-EDTA
Agarose 1.5% (w/v)
Ethidiumbromide 0.5 μg/ml

The invention claimed is:

1. A method for providing a cytoplasmic male sterile *Petroselinum crispum* plant, comprising:
   (a) pollinating a cytoplasmic male sterile *Foeniculum vulgare* Mill. plant with pollen from a monoecious *Petroselinum crispum* plant, wherein said *Foeniculum vulgare* plant has deposit number NCIMB 42055,
   (b) obtaining seeds produced on the male sterile *Foeniculum vulgare* plant,
   (c) growing a cytoplasmic male sterile plant from the seeds of step (b),
   (d) pollinating the plant of step (c) with pollen from a monoecious *Petroselinum crispum* plant, to obtain seeds produced on the plant of step (c), and
   (e) growing a hybrid cytoplasmic male sterile *Petroselinum crispum* plant from the seeds of step (d).

2. The method of claim 1, further comprising:
   (f) pollinating the cytoplasmic male sterile plant of step (e) with pollen from the monoecious *Petroselinum crispum* plant of step (d), to obtain seeds produced on the plant of step (e),
   (g) growing a cytoplasmic male sterile plant from the seeds of step (f),
   (h) pollinating the cytoplasmic male sterile plant of step (g) with pollen from the monoecious *Petroselinum crispum* plant of step (d), obtaining seeds produced on the plant of step (g), and growing a cytoplasmic male sterile *Petroselinum crispum* plant from said seeds; and
   (i) optionally repeating step (h) for at least one generation; thereby obtaining an inbred cytoplasmic male sterile *Petroselinum crispum* plant.

3. The method of claim 1, wherein the monoecious *Petroselinum crispum* plant is a *Petroselinum crispum* var. *tuberosum* plant with deposit number NCIMB 42056.

4. The method of claim 2, wherein the monoecious *Petroselinum crispum* plant is a *Petroselinum crispum* var. *tuberosum* plant with deposit number NCIMB 42056.

5. A cytoplasmic male sterile *Petroselinum crispum* plant obtained by the method of claim 1.

6. A cytoplasmic male sterile *Petroselinum crispum* plant obtained by the method of claim 2.

* * * * *